United States Patent [19]

Soll

[11] Patent Number: 5,559,150

[45] Date of Patent: Sep. 24, 1996

[54] N,N-DISULFONYLATED AMINOBENZENE CARBOXLIC ACIDS AND THE USE THEREOF AS THROMBIN INHIBITORS

[75] Inventor: Richard M. Soll, Lawrenceville, N.J.

[73] Assignee: 3-Dimensional Pharmaceuticals, Inc., Exton, Pa.

[21] Appl. No.: 470,578

[22] Filed: Jun. 6, 1995

[51] Int. Cl.$^6$ .................. A61K 31/19; C07C 317/26; C07C 311/21; C07D 213/42

[52] U.S. Cl. .................. 514/562; 514/357; 514/471; 514/438; 514/415; 514/427; 514/522; 514/601; 514/604; 514/605; 546/338; 549/75; 549/491; 548/503; 548/507; 548/561; 562/430; 564/82; 558/394

[58] Field of Search .................. 562/430; 564/82; 514/601, 604, 562, 357, 471, 438, 415, 427, 522; 558/394; 546/338; 549/491, 75; 548/503, 507, 561

[56] References Cited

U.S. PATENT DOCUMENTS

| | | | |
|---|---|---|---|
| 5,086,065 | 2/1992 | Konno et al. | 514/372 |
| 5,110,812 | 5/1992 | Han | 514/210 |
| 5,248,673 | 9/1993 | Balasubramanian et al. | 514/212 |

FOREIGN PATENT DOCUMENTS

| | | |
|---|---|---|
| WO93/15756 | 8/1993 | WIPO . |
| WO94/20468 | 9/1994 | WIPO . |
| WO94/20526 | 9/1994 | WIPO . |

OTHER PUBLICATIONS

Yagupol'skii et al., Chemical Abstracts, @1974, 81:25298p.

Church and Hoffman, Heparin Cofactor II and Thrombin: Hepartin–Binding Proteins Linking Haemostasis and Inflammation, *Trends in Cardiovascular Medicine* 4(3):140–146 @1994.

Claeson G., Synthetic peptides and peptidomimetics as substrates and inhibitors of thrombin and other proteases in the blood coagulation system, *Blood Coagulation and Fibrinolysis* 5:411–436 (Jun. 1994).

Coughlin S. R., Molecular Mechanisms of Thrombin Signaling, *Seminars in Hematology* 31(4):270–277 (Oct. 1994).

Harker L. A., Strategies for inhibiting the effects of thrombin, *Blood Coagulation and Fibrinolysis* 5 (Suppl 1):S47–S58 (Jan. 1994).

Lefkovits and Topol, Direct Thrombin Inhibitors in Cardiovascular Medicine, *Circulation* 90(3):1522–1536 (Sep. 1994).

Raj et al., Long–term Oral Anticoagulant Therapy:Update on Indicators, Therapeutic Ranges, and Monitoring, *The American Journal of the Medical Sciences* 307(2):128–32 (Feb. 1994).

Tapparelli et al., Synthetic low–molecular weight thrombin inhibitors:molecular design and pharmacological profile, *Trends in Pharmacological Sciences* 14:366–376 Oct. (1993).

Weitz and Hirsh, New Anticoagulant Strategies, *Journal of Laboratory Clinical Medicine* 122:364–373 Oct. (1993).

*Primary Examiner*—Johann Richter
*Assistant Examiner*—Laura L. Stockton
*Attorney, Agent, or Firm*—Sterne, Kessler, Goldstein & Fox, P.L.L.C.

[57] ABSTRACT

The present invention is directed to novel compounds that are non-peptidic thrombin inhibitors. The compounds have the structure:

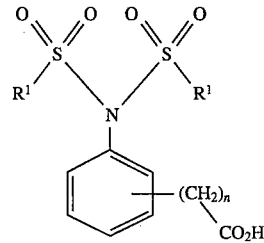

and pharmaceutically acceptable salts thereof; wherein $R^1$ is one of alkyl, substituted alkyl, cycloalkyl, aryl, substituted aryl, heteroaryl or substituted heteroaryl; and n is from zero to five. The compounds of the invention are useful for the treatment of arterial and venous thrombotic occlusive disorders, inflammation, cancer, and neurodegenerative diseases.

13 Claims, No Drawings

N,N-DISULFONYLATED AMINOBENZENE CARBOXLIC ACIDS AND THE USE THEREOF AS THROMBIN INHIBITORS

FIELD OF THE INVENTION

The present invention relates to novel compounds that are non-peptidic inhibitors of thrombin activity, their pharmaceutically acceptable salts, and pharmaceutical compositions thereof. The compounds are useful in the treatment of arterial and venous thrombotic occlusive disorders, inflammation, cancer and neurodegenerative disease.

BACKGROUND OF THE INVENTION

The serine protease thrombin occupies a central role in hemostasis and thrombosis (Tapparelli et al., *Trends in Pharmacological Sciences* 14:366–376 (1993); Lefkovits and Topol, *Circulation* 90(3):1522–1536 (1994); Harker, *Blood Coagulation and Fibrinolysis* 5 (Suppl 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism.

As a multifactorial protein, thrombin induces a number of effects on platelets, endothelial cells, smooth muscle cells, leukocytes, the heart, and neurons (Tapparelli et al., *Trends in Pharmacological Sciences* 14:366–376 (1993); Church and Hoffman, *Trends in Cardiovascular Medicine* 4(3):140–146 (1993)). Platelet activation leads to shape change and aggregation as well as the synthesis, release and secretion of vasoactive substances and lysosomal enzymes. Endothelial cell activation results in the secretion of stimulatory agents leading to increased vascular permeability and adhesiveness for mononuclear cells, one consequence of which is extravasation of leukocytes at the site of thrombin generation. Thrombin induces fibroblast and smooth muscle cell proliferation suggesting that thrombin plays a key role in lesion development following vascular damage. Enhanced automaticity and prolongation of repolarization have been observed in cardiac myocytes showing sensitivity to thrombin. Normal neuronal development has been shown also to be influenced by thrombin. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoaguability during chemotherapy; Alzheimer's disease; and Down's syndrome.

To date only three classes of compounds (heparins, low-molecular weight heparins and coumarins, such as warfarin) have been used in anticoagulant therapy. Each class has severe limitations and liabilities (Weitz and Hirsh, *Journal of Laboratory Clinical Medicine* 122:364–373 (1993); Raj et al., *The American Journal of the Medical Sciences* 307(2):128 (1994)). All three classes indirectly inhibit thrombin. Heparin and low-molecular weight heparins augment antithrombin III and/or heparin cofactor II inhibition of thrombin, whereas coumarins inhibit vitamin K-dependent post-translational modifications. Close monitoring and titration of therapeutic doses is required when employing these agents due to patient variability. Hemorrhagic complications due to bleeding are an encountered side effect. In fact, bleeding remains as the most common side effect of long term oral anticoagulant therapy. Lack of activity in arterial thrombosis in the case of heparin is due to its inability to inhibit clot bound thrombin. Lack of oral activity in the case of heparins and low-molecular weight heparins preclude their use for chronic administration.

Direct thrombin inhibitors of various structural classes have been identified recently (Tapparelli et al., *Trends in Pharmacological Sciences* 14:366–376 (1993); Claeson, *Blood Coagulation and Fibrinolysis* 5:411–436 (1994); Lefkovits and Topol, *Circulation* 90(3):1522–1536 (1994)). Representative compounds that act by inhibiting the active site of thrombin include the α-chloroketone D-phenylalanyl-L-prolyl-L-arginyl chloromethylketone (PPACK), the boroarginine DUP714, the peptide arginal GYK114766, the cyclic peptides cyclotheonamides A and B, the benzamidine NAPAP, and the arylsulphonylarginine argatroban. The thrombin inhibitory peptides hirudin and hirulogs additionally span through the active and exosite domains of thrombin. The peptide hirugen and single-stranded DNA aptamers inhibit thrombin through exosite occupancy.

Experimental studies with direct thrombin inhibitors have shown efficacious antithrombotic effects in various animal models (Lefkovits and Topol, *Circulation* 90(3):1522–1536 (1994)). Direct thrombin inhibitors may take on an important adjunctive role in thrombolysis and may offer a beneficial role in the field of coronary intervention. Clinical studies with direct thrombin inhibitors for treating acute myocardial infarction, for treating unstable angina, and for patients undergoing diagnostic coronary angiography have provided encouraging results. Nevertheless, these classes of antithrombotic agents still suffer from one or more of the following liabilities: (1) poor oral bioavailability due to the peptidic or oligonucleotidic nature of these agents, or high molecular weight or charged nature of the agents; (2) potential for bleeding complications; (3) poor selectivity towards thrombin versus other serine proteases (which may lead to severe and sometimes fatal hypotension and respiratory depression in animal models); (4) liver toxicity; or (5) cost effectiveness.

A need continues to exist for non-peptidic compounds that are potent and selective inhibitors of thrombin, and which possess greater bioavailability and fewer side-effects than currently available direct inhibitors of thrombin.

U.S. Pat. No. 5,248,673, issued Sep. 28, 1993, discloses bisamidine derivatives as thrombin inhibitors. The patent discloses that these compounds can be used in the treatment of thrombosis, ischemia and stroke.

PCT Published Application WO 93/15756, published Aug. 19, 1993, discloses peptide aldehyde analogs that exhibit thrombin inhibiting activity.

PCT Published Application WO 94/20526, published Sep. 15, 1994, discloses peptide derivatives having a C-terminal boronic acid group. The published application discloses that these peptides possess protease-inhibiting activity and are potent thrombin inhibitors.

PCT Published Application WO 94/20468, published Sep. 15, 1994, discloses 4-aminopyridine derivatives and discloses that these derivatives have thrombin inhibitory activity.

U.S. Pat. No. 5,110,812, issued May 5, 1992, discloses 3-guanidinoalkylazetidin-2-one derivatives as serine protease inhibitors. The patent discloses that these compounds exhibit anti-thrombin and anti-trypsin activities.

U.S. Pat. No. 5,086,065, issued Feb. 4, 1992, discloses phenylalkan(en)oic acids exhibiting antagonistic activity on leukotriene $B_4$. Included within the large class of acids are propionic acids having the following formulae:

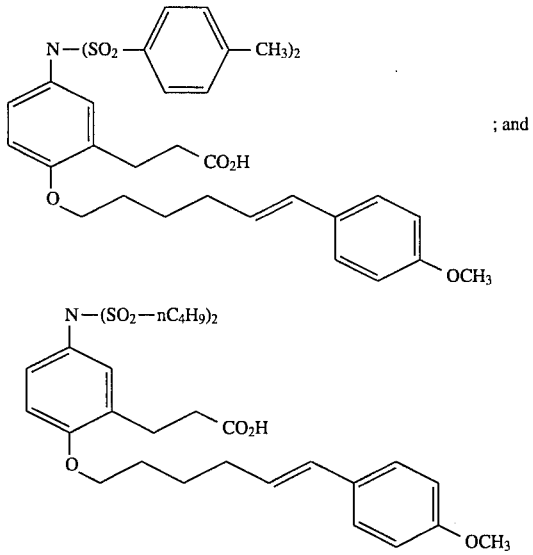

SUMMARY OF THE INVENTION

The present invention is directed to novel N,N-disulfonylated aminobenzoic acids, N,N-disulfonylated aminobenzenealkanoic acids, and pharmaceutically acceptable salts thereof. The novel compounds have the general Formula I (below). Also provided is a process for preparing compounds of Formula I. The novel compounds of the present invention exhibit antithrombotic activity via direct inhibition of thrombin. Also provided is a method of treating thrombosis, ischemia, stroke, restenosis or inflammation lo in a mammal in need of such treatment comprising administering to said mammal an effective amount of a compound of Formula I. Further provided is a pharmaceutical composition comprising a compound of Formula I and one or more pharmaceutically acceptable carriers or diluents.

DETAILED DESCRIPTION OF THE PREFERRED EMBODIMENTS

The present invention is directed to compounds of Formula I:

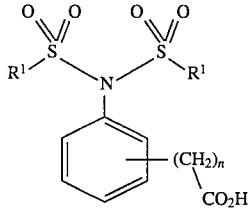

and pharmaceutically acceptable salts thereof;
wherein
each $R^1$ is independently one of alkyl, substituted alkyl, cycloalkyl, aryl, substituted aryl, heteroaryl or substituted heteroaryl;

n is from zero to five; and
the substituent $-(CH_2)_n-CO_2H$ is ortho-, meta- or para- to the N,N-disulfonylamino group.

The N,N-disulfonylated amino group may be in the ortho-, meta- or para- position relative to the acid group, with meta- being preferred.

When $R^1$ is heteroaryl or substituted heteroaryl, preferred heteroaryl groups include pyridinyl, thienyl, chromenyl, benzoxazolyl, quinazolinyl, quinolinyl and tetrahydroquinolinyl. Preferred groups when $R^1$ is substituted heteroaryl include those heteroaryl groups mentioned as preferred, having one or more substituents selected from halogen, $C_{1-6}$alkyl, $C_{1-6}$alkoxy, carboxy, amino, $C_{1-6}$alkylamino and/or di($C_{1-6}$)alkylamino.

Preferred compounds within the scope of the present invention include those of Formula I wherein each $R^1$ is independently one of $C_{1-7}$alkyl, $C_{6-10}$aryl or $C_{6-10}$aryl substituted with halogen, hydroxy, amino, nitro, cyano, arylalkyl or heteroarylalkyl; and n is from zero to 5, more preferably zero, 1, 2 or 3, and most preferably zero or 1.

Suitable arylalkyl groups that may be employed as optional substituents on the phenyl, naphthyl and tetrahydronaphthyl groups of $R^1$ include $C_{6-10}$ aryl($C_{1-6}$)alkyl, preferably $C_{6-10}$10aryl($C_{1-3}$)alkyl. Useful optional arylalkyl substituents include benzyl, phenethyl, phenylpropyl, naphthylmethyl and naphthylethyl. Suitable heteroarylalkyl groups that may be employed as optional substituents on the phenyl, naphthyl and tetrahydronaphthyl groups of $R^1$ include $C_{3-8}$heteroaryl($C_{1-6}$)alkyl, preferably $C_{3-8}$heteroaryl($C_{1-3}$)alkyl. Useful optional heteroarylalkyl substituents include pyridylmethyl, pyridylethyl, furanylmethyl, furanylethyl, indolylmethyl, indolylethyl, thiofuranylmethyl and thiofuranylethyl. There may be up to three optional substituents on the $R^1$ aryl group, preferably one or two substituents.

More preferred are compounds of Formula I wherein each $R^1$ is the same and is one of $C_{1-7}$alkyl, $C_{6-10}$aryl or $C_{6-10}$aryl substituted with one or more of halogen, hydroxy, amino, nitro, cyano or $-(CH_2)_p-R^2$; $R^2$ is one of phenyl, naphthyl, pyridinyl, furanyl, thiofuranyl, indole or pyrrole; p is one or two; and n is from zero to five.

Even more preferred are compounds of Formula I wherein each $R^1$ is the same and is one of $C_{1-7}$alkyl, phenyl, naphthyl or tetrahydronaphthyl, and n is from zero to five, preferably zero, 1, 2 or 3, most preferably zero or 1.

Most preferred compounds of the present invention include compounds of Formula I wherein each $R^1$ is the same and is one of $C_{1-7}$alkyl, phenyl, naphthyl or tetrahydronaphthyl, and n is from zero to five, preferably zero, 1, 2 or 3, most preferably zero or 1.

A most preferred compound of the present invention is 2-[bis[(2-naphthyl)sulfonyl]amino]benzoic acid, having the structure:

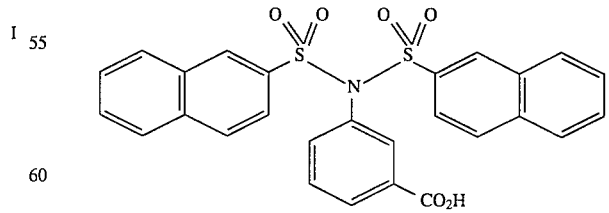

A second preferred Compound is 2-[bis[phenylsulfonyl]amino]benzoic acid.

The term "alkyl" as employed herein includes both straight and branched chain radicals of up to 12 carbons, preferably 1-7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the various branched chain isomers thereof.

The term "substituted alkyl" as employed herein includes alkyl groups, as defined above that have one, two or three halo substituents, or one $C_{6-10}$aryl, $C_{1-6}$alkyl($C_{6-10}$)aryl, halo($C_{6-10}$)aryl, $C_{3-8}$cycloalkyl, $C_{1-6}$alkyl($C_{3-8}$)cycloalkyl, $C_{2-8}$alkenyl, $C_{2-8}$alkynyl, hydroxy, amino, nitro, cyano and/or carboxy.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

Typical heteroaryl groups have 3 to 14 ring atoms; 6, 10 or 14 π electrons shared in a cyclic array; and contain carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The terms "substituted aryl" and "substituted heteroaryl" as employed herein includes aryl and heteroaryl groups, as defined above, that include one or two substituents on the aromatic ring(s), such as $C_{1-6}$alkyl, $C_{3-8}$cycloalkyl, $C_{1-6}$alkyl($C_{3-8}$)cycloalkyl, $C_{2-8}$alkenyl, $C_{2-8}$alkynyl, cyano, amino, $C_{1-6}$alkylamino, di($C_{1-6}$)alkylamino, benzylamino, dibenzylamino, nitro, carboxy, carbo($C_{1-6}$)alkoxy, trifluoromethyl, halogen, $C_{1-6}$alkoxy, $C_{6-10}$aryl($C_{1-6}$)alkoxy, hydroxy, $C_{1-6}$alkylthio, $C_{1-6}$alkylsulfinyl, $C_{1-6}$alkylsulfonyl, $C_{6-10}$arylthio, $C_{6-10}$arylsulfinyl, $C_{6-10}$arylsulfonyl, $C_{6-10}$aryl($C_{1-6}$)alkyl and/or ($C_{3-8}$heteroaryl ($C_{1-6}$)alkyl.

The term "aralkyl" or "arylalkyl" as used herein by itself or as part of another group refers to $C_{1-6}$alkyl groups as discussed above having an aryl substituent, such as benzyl.

The term "halogen" or "halo" as used herein by itself or as part of another group refers to chlorine, bromine, fluorine or iodine with chlorine being preferred.

The term "cycloalkyl" as employed herein includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy group.

The terms "alkoxy," or "aralkoxy" includes any of the above alkyl or aralkyl groups linked to an oxygen atom.

The term "alkenyl" by itself or as part of another group as employed herein includes a carbon chain by itself or as part of another group of up to 16 carbons, preferably 2 to 10 carbons, containing one double bond such as propenyl, 2-butenyl, 3-butenyl, 2-pentenyl, 4-pentenyl and the like, and may include a halogen substituent such as I, Cl, or F.

The term "alkynyl" by itself or as part of another group as employed herein includes a carbon chain of up to 16 carbons, preferably 2 to 10 carbons, containing one triple bond such as 2-propynyl, 2-butynyl, 3-butynyl and the like.

The compounds of the present invention may be prepared by standard techniques as outlined in Scheme I.

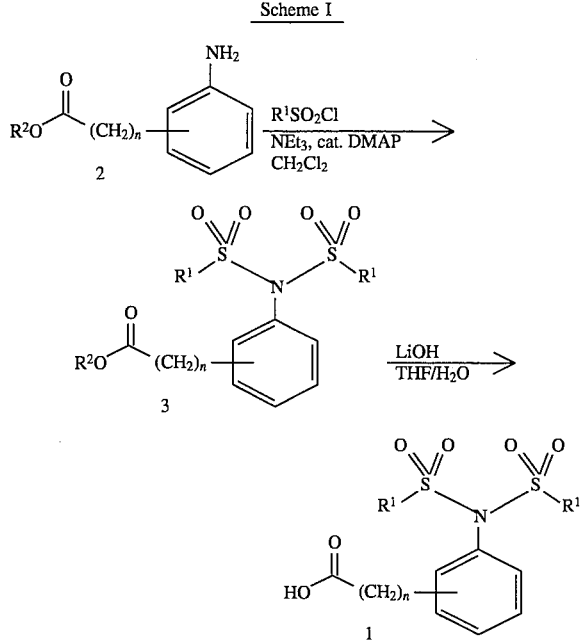

Scheme I wherein $R^1$ and n are defined as above. $R^2$ is a $C_{1-6}$ alkyl group.

Treatment of an aminophenalkanoic acid ester 2 with an appropriate sulfonyl chloride in the presence of an amine base, such as triethylamine, and a catalytic amount N,N-dimethylaminopyridine (DMAP) in a polar organic solvent at ambient temperature provides disulfonylated derivative 3. Useful solvents include methylene chloride, tetrahydrofuran, acetonitrile, and dimethylformamide. Hydrolysis of 3 with an aqueous hydroxide, such as lithium hydroxide, in a polar organic solvent, such as tetrahydrofuran, at ambient temperature provides the compounds 1 of the present invention.

Compounds having two different $R^1$ moieties can be formed by first treating the ester 2 with one molar equivalent of a first sulfonyl chloride to form a mono-sulfonylated intermediate. This initial step requires substituting a weaker base, such as N-methylmorpholine, for the triethylamine and DMAP employed in the general scheme. The mono-sulfonylated intermediate is thereafter reacted with a second sulfonyl chloride having a different $R^1$ substituent to form the unsymmetrical product. The second sulfonylation step is performed in the presence of a stronger base, such as triethylamine and DMAP. A separation step, such as high performance liquid chromatography (HPLC), can be performed to separate any symmetrical products from the desired unsymmetrical product.

Compounds having the N,N-disulfonylated moiety in the ortho- or para- position can be formed by employing commercially available anthranilic acid methyl ester or methyl p-aminobenzoate.

Also included within the scope of the present invention are non-toxic pharmaceutically acceptable salts of the compounds of Formula I. Basic salts are formed by mixing a solution of a particular compound of the present invention with a solution of a pharmaceutically acceptable non-toxic base, such as, sodium hydroxide, potassium hydroxide, sodium bicarbonate, sodium carbonate, or an amino compound, such as choline hydroxide, Tris, bis-Tris, N-methylglucamine or arginine. Water-soluble salts are preferable.

Thus, suitable salts include: alkaline metal salts (sodium, potassium etc.), alkaline earth metal salts (magnesium, calcium etc.), ammonium salts and salts of pharmaceutically acceptable amines (tetramethylammonium, triethylamine, methylamine, dimethylamine, cyclopentylamine, benzylamine, phenethylamine, piperidine monoethanolamine, diethanolamine, tris(hydroxymethyl)amine, lysine, arginine and N-methyl-D-glucamine).

The compounds of the present invention are distinguished by their ability to preferentially inhibit thrombin in comparison to other serine proteases such as plasmin. As thrombin inhibitors, the compounds of the present invention inhibit thrombin function. Therefore, the compounds are useful for the treatment or prophylaxis of states characterized by abnormal venous or arterial thrombosis involving either thrombin production or action. These states include, but are not limited to, deep vein thrombosis; disseminated intravascular coagulpathy which occurs during septic shock, viral infections and cancer; myocardial infarction; stroke; coronary artery bypass; hip replacement; thrombus formation resulting from either thrombolytic therapy or percutaneous transluminal coronary angioplasty (PCTA). The compounds of the present invention may also be used as an anticoagulant in extracorporeal blood circuits. By virtue of the effects of thrombin on a host of cell types such as smooth muscle cells, endothelial cells and neutrophils, the compounds of the present invention find additional use in the treatment or prophylaxis of adult respiratory ,distress syndrome; inflammatory responses such as edema; reperfusion damage; atherosclerosis; and restenosis following injury such as balloon angioplasty, atherectomy and arterial stent placement.

The compounds of the present invention may be useful in treating neoplasia and metastasis as well as neurodegenerative diseases, such as Alzheimer's disease and Parkinson's disease.

The compounds of the present invention may be used in combination with thrombolytic agents such as tissue plasminogen activator, streptokinase and urokinase. Additionally, the compounds of the present invention may be used in combination with other antithrombotic or anticoagulant drugs such as, but not limited to, fibrinogen antagonists and thromboxane receptor antagonists.

The .compounds of the present invention may be administered in an effective amount within the dosage range of about 0.1 to 500 mg/kg, preferably between 0.1 to 10 mg/kg body weight, on a regimen in single or 2–4 divided daily doses.

The pharmaceutical compositions of the invention can be administered to any animal that can experience the beneficial effects of the compounds of the invention, Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, crosslinked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts and alkaline solutions. Especially preferred alkaline salts are ammonium salts prepared, for example, with Tris, choline hydroxide, Bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG- 400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention.

Other suitable modifications and adaptations of the variety of conditions and parameters normally encountered and obvious to those skilled in the art are within the spirit and scope of the invention.

EXAMPLE 1

Preparation of Methyl 3-Aminobenzoate (4)

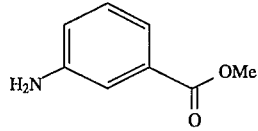

A mixture of methyl 3-nitrobenzoate (18.1 g, 0.10 mmol) in ethanol/tetrahydrofuran (9:1) and 1.8 g of 10% Pd/C was hydrogenated under a hydrogen atmosphere at atmospheric pressure and ambient temperature for 24 hr. The reaction mixture was filtered through Celite (Celite is a registered trademark of the John-Manville Product Corporation for diatomaceous earth) and washed with ethanol. The solvent was removed in vacuo to give the title compound as a pale yellow solid (14.7 g; 97% yield) which was used without further purification in the next reaction. $^1$H-NMR (200 MHz; CDCl$_3$) δ7.43 (d, 1H, J=7.6 Hz), 7.35 (t, 1H, J=2.3 Hz), 7.25 (d, 1H, J=2.3 Hz), 7.19 (d, 1H, J=7.7 Hz), 3.89 (s, 3H), 3.7 (bs, 2H).

EXAMPLE 2

Methyl 3-[(2-Naphthalenyl)sulfonylamino]benzoate (5)

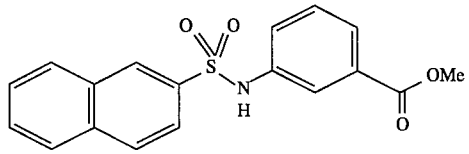

To 5.0 g (33 mmol) of methyl 3-aminobenzoate (4) in 70 mL of methylene chloride containing 4.0 mL (36 mmol) of N-methylmorpholine was added 7.49 g (33 mmol) of 2-naphthalenesulfonyl chloride. After stirring at room temperature overnight, the reaction mixture was quenched with 1N HCl (100 mL). The suspension was dissolved in ca. 250 mL of tetrahydrofuran and enough ether was added to induce phase separation. The organic extract was washed with saturated sodium chloride solution (2×). The organic phase was dried (MgSO$_4$), and concentrated to give 11.0g (97% yield) of the title compound as a pale yellow solid: $^1$H-NMR (200 MHz; DMSO-d$_6$) δ8.46 (s, 1H), 8.13 (t, 2H), 7.99 (d, 1H), 7.55–7.75 (m, 5H), 7.43 (dd, 21H), 7.38 (d, 1H), 3.79 ppm (s, 3H).

EXAMPLE 3

Preparation of Methyl 3-[Bis[(2-naphthalenyl)sulfonyl]amino]benzoate (7)

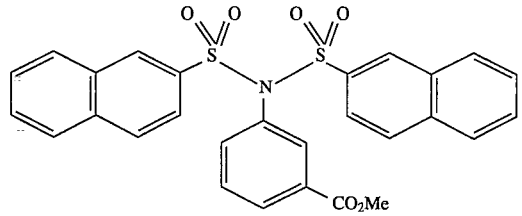

To 1.0 g of methyl 3-aminobenzoate (6) (6.62 mmol) in 10 mL of tetrahydrofuran containing 2 mL (14.4 mmol) of triethylamine was added 1.58 g (6.96 mmol) of 2-napthalenesulfonyl chloride. After 10 min, 100 mg of N,N-dimethylaminopyridine was added. After 15 min, another 600 mg of 2-napthalenesulfonyl chloride was added. After stirring for 30 min, the reaction mixture was quenched with 2N HCl and then extracted into ether. The ethereal phase was washed sequentially with water and saturated NaHCO$_3$, then dried (MgSO$_4$), concentrated, and triturated with ether/petroleum ether to give 2.6 g of the title compound as a colorless powder: $^1$H-NMR (CDCl$_3$, 200 MHz) δ8.46 (s, 2H), 8.13 (d, 1H, J=7.8 Hz), 7.92–8.04 m, 8H), 7.59–7.75 (m, 5H), 7.42 (t, 1H, J=8 Hz), 7.22 (d, 1H, J=7.6 Hz), 3.80 (s, 3H).

EXAMPLE 4

Preparation of 3-[Bis[(2-naphthalenyl)sulfonyl]amino]benzoic Acid (8)

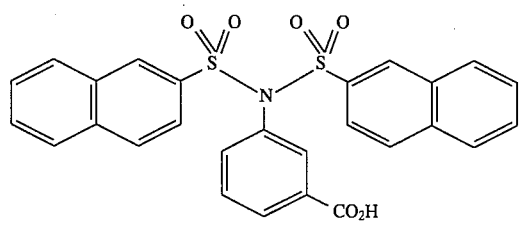

A solution of 770 mg (1.45 mmol) of the compound prepared in Example 3 (7) in THF/H$_2$O (ca. 50 mL; 9:1) and 35 mg (1.45 mmol) of lithium hydroxide was stirred at ambient temperature for 2 h. Another 73 mg of lithium hydroxide was added and the compound was then stirred at room temperature for 1 h. The reaction mixture was diluted with water (20 mL) and ether (100 mL). The suspension was acidified with 1N HCl. The organic phase was dried (MgSO$_4$) and concentrated. Trituration with ether/hexane gave 554 mg (74%) of a colorless solid: $^1$H-NMR (DMSO-d6; 300 MHz) δ13.29 (bs, 2H), 8.49 (d, 2H, J=1.6 Hz), 8.26 (d, 2H, J=7.8 Hz), 8.16 (t, 4H, J=7.6 Hz), 8.06 (d, 1H, J=7.9 Hz), 7.7–7.86 (m, 6H), 7.59 (t, 1H, J=6.8 Hz 7.54 (t, 1H, J=1.8 Hz), 7.39 (br d, 1H, J=7.6 Hz). Mass Spectrum calcd. for C$_{27}$H$_{19}$NO$_6$S$_2$:540.0 (M+Na). Found: 540.1 (using gentisic acid matrix).

EXAMPLE 5

Preparation of 3-[Bis(phenylsulfonyl)amino]benzoic Acid

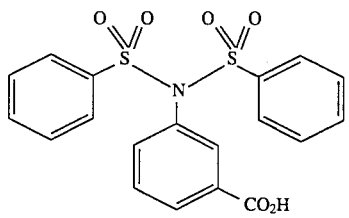

The title compound was prepared in a manner identical to that of Examples 3 and 4 in which phenylsulfonyl chloride replaced 2-napthalenesulfonyl chloride. Mass Spectrum (MALDI-TOF; gentisic acid matrix) calcd. for $C_{19}H_{15}NO_6S_2$: 440.0 (M+Na) 456.0 (M+K). Found: 439.5, 455.4.

EXAMPLE 6

In Vitro Inhibition of Purified Enzymes

All assays are based on the ability of the test compound to inhibit the hydrolysis of a peptide p-nitroanilide substrate. In a typical experiment, substrate is prepared in DMSO, and diluted into an assay buffer consisting of 50 mM HEPES, 130 mM NaCl, pH 7.5. The final concentration for each of the substrates is listed below. All substrate concentrations are at least 10-fold lower than $K_m$ to insure inhibition is competitive. Test compounds are prepared as a 1 mg/ml solution in DMSO, and 3 additional 10-fold dilutions in DMSO are prepared. Enzyme solutions are prepared at the concentrations listed below in assay buffer.

In a typical $IC_{50}$ determination, into each well of a 96 well plate is pipetted 280 uL of substrate solution, 10 μL of inhibitor solution, and the plate allowed to thermally equilibrate at 37° C. in a Molecular Devices Plate Reader for >10 minutes. Reactions were initiated by the addition of a 20 μL aliquot of enzyme, and the absorbance increase at 405 nm is recorded for 15 minutes. Data corresponding to less than 10% of the total substrate hydrolysis was used in the calculations. The ratio of the velocity (rate of the change in absorbance as a function of time) for a sample containing no inhibitor is divided by the velocity of a sample containing inhibitor, and is plotted as a function of inhibitor concentration. The inverse of the slope is the concentration of inhibitor which produces a 50% decrease in activity of the enzyme. This concentration is referred to as the $IC_{50}$.

Thrombin

Thrombin activity was assessed as the ability to hydrolyse the substrate N-benzoyl-Phe-Val-Arg-p-nitroaniline (Bz-Phe-Val-Arg-pNa), and was obtained from Sigma Chemical Co., St. Louis, Mo. Substrate solutions were prepared at a concentration of 60 μM (60 μM<<$K_m$=1.2 mM) in assay buffer. Final DMSO concentration was 0.3%. Purified human α-thrombin was obtained from Enzyme Research Laboratories Inc., and was diluted into assay buffer to a concentration of 1.2 μM. Final reagent concentrations were: [thrombin]=36 nM, [Bz-Phe-Val.-Arg-pNa]=66 μM, [inhibitor]=60 to 0.06 μM.

Factor Xa

Factor Xa activity was assessed as the ability to hydrolyse the substrate Bz-Ile-Glu-Gly-Arg-pNa (obtained from Sigma Chemical Company, St Louis, Mo.). Substrate solutions were prepared at a concentration of 26 μM (26 μM<<$K_m$=1.3 mM) in assay buffer. Final DMSO concentration was 0.3%. Activated Factor Xa was obtained from Enzyme Research Laboratories Inc., and was diluted into assay buffer to a concentration of 1.2 μM. Final reagent concentrations were: [Factor Xa]=10 nM, [Bz-Ile-Glu-Gly-Arg-pNa]=26 μM, [inhibitor]=60 to 0.06 μM.

Plasmin

Plasmin activity was assessed as the ability to hydrolyse the substrate Tos-Gly-Pro-Lys-pNa, obtained from Sigma. Substrate solutions were prepared at a concentration of 22 μM (22 μM<<$K_m$=240 μM) in assay buffer. Final DMSO concentration was 0.3%. Purified human plasmin was obtained from Enzyme Research Laboratories Inc., and was diluted into assay buffer to a concentration of 1.2 μM. Final reagent concentrations were: [plasmin]=15 nM, [Bz-Ile-Glu-Gly-Arg-pNa]=26 μM, [inhibitor]=60 to 0.06 μM.

Table 1 below gives the $IC_{50}$ values for the compound of Example 4.

TABLE 1

| Compound of Example # | Thrombin Inhibition $IC_{50}$ (μM) | Factor Xa Inhibition $IC_{50}$ (μM) | Plasmin Inhibition $IC_{50}$ (μM) |
|---|---|---|---|
| 4 | 0.8 | 59 | 44 |

The results indicate that the compounds of the present invention, and specifically the compound of Example 4, are selective and highly potent inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the formula:

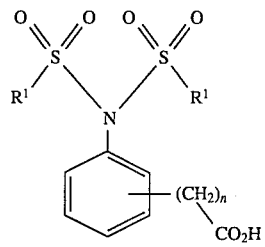

and pharmaceutically acceptable salts thereof;
wherein
each $R^1$ is independently one of alkyl; alkyl substituted by one or two halo substituents, or by one; of $C_{6-10}$aryl, $C_{1-6}$alkyl($C_{6-10}$)aryl, halo($C_{6-10}$)aryl, $C_{3-8}$cycloalkyl, $C_{1-6}$alkyl($C_{3-8}$)cycloalkyl, $C_{2-8}$alkenyl, $C_{2-8}$alkynyl, hydroxy, amino, nitro, cyano or carboxy; cycloalkyl; aryl; substituted aryl; heteroaryl; or substituted heteroaryl;

n is from zero to five; and
the substituent —$(CH_2)_n$—$CO_2H$ is ortho-, meta- or para- to the N,N-disulfonylamino group.

2. A compound according to claim 1 wherein
each $R^1$ is independently one of $C_{1-7}$alkyl, $C_{6-10}$aryl or $C_{6-10}$aryl substituted with one or more of halogen, hydroxy, amino, nitro, cyano, $C_{6-10}$aryl($C_{1-6}$)alkyl or $C_{3-8}$heteroaryl($C_{1-6}$)alkyl; and n is from zero to five.

3. A compound according to claim 2 wherein
n is zero, 1, 2 or 3.

4. A compound according to claim 1 wherein
each $R^1$ is independently one of $C_{1-7}$alkyl, $C_{6-10}$aryl or $C_{6-10}$aryl substituted with one or more of halogen, hydroxy, amino, nitro, cyano, benzyl, phenethyl, naphthylmethyl, naphthylethyl, pyridylmethyl, pyridylethyl, furanylmethyl, furanylethyl, thiofuranylmethyl, thiofuranylethyl, idolylmethyl, indolylethyl, pyrrolylmethyl or pyrrolylethyl; and
n is from zero to five.

5. A compound according to claim 1 wherein each $R^1$ is the same and one of alkyl, phenyl or naphthyl; and
n is from zero to five.

6. A compound according to claim 5 wherein N is zero, 1, 2 or 3.

7. A compound according to claim 5 wherein each $R^1$ is the same and is 2-naphthyl; and n is zero or 1.

8. A compound according to claim 7 which is 2-[bis[(2-naphthalenyl)sulfonyl]amino]benzoic acid.

9. A pharmaceutical composition comprising a compound of claim 1.

10. A pharmaceutical composition of claim 9 further comprising a pharmaceutically acceptable carrier or diluent.

11. A method of treating thrombosis, ischemia, stroke, restenosis or inflammation comprising administering to a mammal in need of said treatment a therapeutically or prophylactically effective amount of a compound of claim 1.

12. A method of treating thrombosis, ischemia, stroke, restenosis or inflammation comprising administering to a mammal in need of said treatment a therapeutically or prophylactically effective amount of a compound of claim 4.

13. A method of treating thrombosis, ischemia, stroke, restenosis or intimation comprising administering to a mammal in need of said treatment a therapeutically or prophylactically effective amount of a compound of claim 8.

* * * * *